United States Patent
Lang et al.

(10) Patent No.: US 10,894,223 B2
(45) Date of Patent: Jan. 19, 2021

(54) PROCESS FOR ISOLATING PURE 2-ETHYLHEXYL ACRYLATE OR PURE 2-PROPYLHEPTYL ACRYLATE FROM THE CORRESPONDING CRUDE ALKYL ACRYLATE BY DISTILLATION

(71) Applicant: BASF SE, Ludwigshafen am Rhein (DE)

(72) Inventors: Ortmund Lang, Ludwigshafen (DE); Bernd Metzen, Ludwigshafen (DE); Claus Hechler, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 16/472,054

(22) PCT Filed: Dec. 11, 2017

(86) PCT No.: PCT/EP2017/082203
§ 371 (c)(1),
(2) Date: Jun. 20, 2019

(87) PCT Pub. No.: WO2018/114429
PCT Pub. Date: Jun. 28, 2018

(65) Prior Publication Data
US 2020/0094160 A1   Mar. 26, 2020

(30) Foreign Application Priority Data
Dec. 21, 2016   (EP) .................................... 16205968

(51) Int. Cl.
*B01D 3/14* (2006.01)
*B01D 3/22* (2006.01)
(Continued)

(52) U.S. Cl.
CPC ............. *B01D 3/141* (2013.01); *B01D 3/225* (2013.01); *B01D 3/4283* (2013.01); *C07C 67/54* (2013.01)

(58) Field of Classification Search
CPC ...... B01D 3/141; B01D 3/225; B01D 3/4283; C07C 67/54
See application file for complete search history.

(56) References Cited

U.S. PATENT DOCUMENTS 2,819,949 A * 1/1958 Keeler .................. C01B 15/013
203/28
H001957 H * 4/2001 Fried .............................. 526/82
(Continued)

FOREIGN PATENT DOCUMENTS

DE       33 02 525 A1   7/1984
DE     102 58 329 A1   7/2003
(Continued)

OTHER PUBLICATIONS

Derwent Summary of CN 104892416 to Zhou published Sep. 9, 2015.*
(Continued)

*Primary Examiner* — Brian A McCaig
(74) *Attorney, Agent, or Firm* — Oblon, McClelland, Maier & Neustadt, L.L.P.

(57) ABSTRACT

Process for isolating pure 2-ethylhexyl acrylate or pure 2-propylheptyl acrylate from the corresponding crude alkyl acrylate by distillation, wherein the process is carried out in a dividing wall column (1) which has separation-active internals and vaporizer (7) and in which a dividing wall (8) is arranged in the longitudinal direction of the column to form an upper joint column region (9), a lower joint column region (14), an inflow section (10, 12) having a side feed (Continued)

Figure 1:
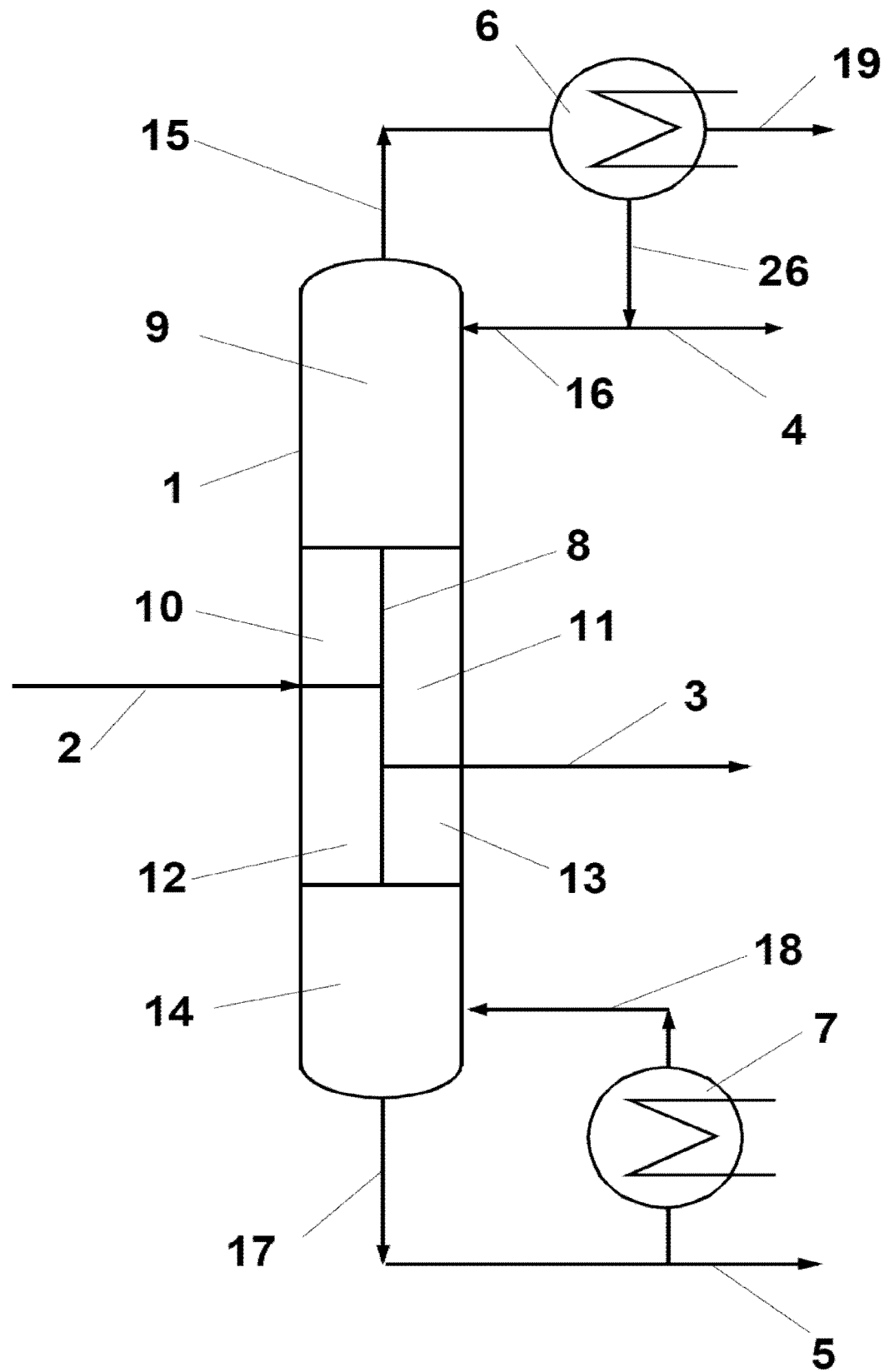

point (2) and an offtake section (11, 13) having a side offtake point (3), the column has a number of theoretical plates in the range from 10 to 60, where the number of theoretical plates of the dividing wall column (1) relates to the sum of the theoretical plates in the joint upper column region (9), the joint lower column region (14) and the inflow section (10, 12), the side feed point (2) for the corresponding crude alkyl acrylate is arranged at a theoretical plate in the region commencing at least two theoretical plates above the bottommost theoretical plate and ending at least two theoretical plates below the uppermost theoretical plate, the side offtake point (3) for the pure 2-ethylhexyl acrylate or pure 2-propylheptyl acrylate is arranged at a theoretical plate in the region commencing at least two theoretical plates above the bottommost theoretical plate and ending at least two theoretical plates below the uppermost theoretical plate and the dividing wall (8) is arranged in the column in the region commencing at least one theoretical plate above the bottommost theoretical plate and ending at least one theoretical plate below the uppermost theoretical plate, where the ratio of amount of liquid at the upper end of the dividing wall (8) going to the enrichment section (10) and the stripping section (11) of the column is set in the range from 1:0.2 to 1:5.

41 Claims, 2 Drawing Sheets

(51) Int. Cl.
*B01D 3/42* (2006.01)
*C07C 67/54* (2006.01)

(56) References Cited

U.S. PATENT DOCUMENTS

| | | |
|---|---|---|
| 2013/0284586 A1 | 10/2013 | Lee et al. |
| 2016/0158667 A1* | 6/2016 | Lee .................. C07C 67/54 203/98 |
| 2019/0016665 A1 | 1/2019 | Tretjak et al. |

FOREIGN PATENT DOCUMENTS

| | | |
|---|---|---|
| DE | 10 2005 053 982 A1 | 5/2006 |
| WO | WO 03/043712 A1 | 5/2003 |
| WO | WO 2017/125657 A1 | 7/2017 |

OTHER PUBLICATIONS

Extended European Search Report dated Jun. 26, 2017 in Patent Application No. 16205968.7, 3 pages.
Kaibel, G. "Distillation Columns with Vertical Partitions" Chemical Engineering Technology, vol. 10, No. 1, 1987, pp. 92-98.
Becker, H. "Polymerisationsinhibierung von (Meth-)Acrylaten", Fachbereich Chemie Technische Universität, 2003, 236 pages (with English abstract).
Kaibel, G. et al. "Möglichkeiten zur Prozeßintegration bei destillativen Trennverfahren" Chemie Ingenieur Technik, vol. 61, No. 2, 1989, pp. 104-112 (with English abstract).
U.S. Appl. No. 15/741,350, filed Jan. 2, 2018, Norbert Asprion.
U.S. Appl. No. 16/472,018, filed Jun. 20, 2019, Ortmund Lang.
U.S. Appl. No. 16/468,823, filed Jun. 12, 2019, Ortmund Lang.
U.S. Appl. No. 16/471,993, filed Jun. 20, 2019, Ortmund Lang.
International Search Report dated Apr. 11, 2018 in PCT/EP2017/082203, citing documents AA and AO therein, 2 pages.

* cited by examiner

PROCESS FOR ISOLATING PURE 2-ETHYLHEXYL ACRYLATE OR PURE 2-PROPYLHEPTYL ACRYLATE FROM THE CORRESPONDING CRUDE ALKYL ACRYLATE BY DISTILLATION

Esters of acrylic acid, $H_2C$=CH—C(=O)OR, will hereinafter also be referred to as acrylates. R is an alkyl radical.

Acrylates such as 2-ethylhexyl acrylate and 2-propylheptyl acrylate are generally obtained industrially by reaction of alcohol (example: 2-ethylhexanol or 2-propylheptanol) and acrylic acid. The synthesis (esterification reaction) forms a product mixture, also referred to as crude acrylate, in which the acrylate generally predominates.

In the present case, R thus corresponds to 2-ethyl hexyl and 2-propylheptyl.

Alkyl acrylates are employed for surface coatings, adhesives, building chemicals, paper coatings and plastics.

In order to meet specification requirements, the crude acrylate obtained in a synthesis has to be purified further by distillation. The specification requirements for pure acrylates provide in particular for, for example, a minimum content of acrylate of 99.5% by weight and a maximum permissible content of acetate, RO(C=O)$CH_3$, of 1500 ppm and of diether, ROR, of 1000 ppm. The isolation of acrylate from the crude acrylate is a complicated distillation problem because of the small differences in the relative volatilities of the components and is therefore generally carried out by means of a two-column arrangement (see below). Owing to the sensitivity of the polymerization-prone acrylates, particular column internals are generally particularly advantageous.

The isolation of acrylate from crude acrylate by distillation is, after a pre-purification which is preferably carried out, e.g. by extraction, carried out in the prior art as is presented, for example, in the thesis "Polymerisationsinhibierung von (Meth-)Acrylaten", TU Darmstadt (Chemistry department), 2003, by Holger Becker on pages 21 to 24 in two distillation columns connected in series:

In a first distillation column, a mixture of predominantly low boilers (relative to the 2-ethylhexyl acrylate or 2-propylheptyl acrylate), e.g., water, alcohol (ROH), acetate (RO(C=O)$CH_3$), diether (ROR), is taken off as overhead product, with the organic low boilers being able to be recirculated to the esterification. At the bottom, the acrylate and the relatively high boilers are separated off. In a second downstream distillation column, the relatively high boilers (relative to the 2-ethylhexyl acrylate or 2-propylheptyl acrylate), e.g. 2-ethylhexyloxy ester or 2-propylheptyloxy ester (ROCH$_2$CH$_2$C(=O)OR), are separated off as bottom product. The desired product (i.e. the pure 2-ethylhexyl acrylate or pure 2-propylheptyl acrylate) is taken off as overhead product from the second distillation column; cf. columns H and I in FIGS. 3-7 on page 24 of the abovementioned thesis. The bottom output from column I is fed to a high boiler separator J (cf. FIGS. 3-7 on page 24 of the abovementioned thesis).

DE 3302525 A1 (BASF AG) and the specialist literature, for example Kaibel et al. in Chem. Eng. Technol. 10 (1987), pages 92 to 98, and in Chem. Ing.-Tech. 61 (1989), No. 2, pages 104 to 112, describe in general terms of the use of dividing wall columns in the purification of organic compounds by distillation.

US 2013/0284586 A1 (LG Chem. Ltd.) describes the use of a dividing wall column for purifying 2-ethylhexyl acrylate by distillation.

In the light of this literature, it was an object of the invention to provide an improved process for the isolation of pure 2-ethylhexyl acrylate or pure 2-propylheptyl acrylate from the respective corresponding crude alkyl acrylate by distillation, which process is, while adhering to the respective specifications for the pure 2-ethylhexyl acrylate and pure 2-propylheptyl acrylate, more economical, in particular in respect of the capital costs and energy costs.

We have accordingly found a process for isolating pure 2-ethylhexyl acrylate or pure 2-propylheptyl acrylate from the corresponding crude alkyl acrylate by distillation, wherein the process is carried out in a dividing wall column (1) which has separation-active internals and vaporizer (7) and in which a dividing wall (8) is arranged in the longitudinal direction of the column to form an upper joint column region (9), a lower joint column region (14), an inflow section (10, 12) having a side feed point (2) and an offtake section (11, 13) having a side offtake point (3), the column has a number of theoretical plates in the range from 10 to 60, the side feed point (2) for the corresponding crude alkyl acrylate is arranged at a theoretical plate in the region commencing at least two theoretical plates above the bottommost theoretical plate and ending at least two theoretical plates below the uppermost theoretical plate, the side offtake point (3) for the pure 2-ethylhexyl acrylate or pure 2-propylheptyl acrylate is arranged at a theoretical plate in the region commencing at least two theoretical plates above the bottommost theoretical plate and ending at least two theoretical plates below the uppermost theoretical plate and the dividing wall (8) is arranged in the column in the region commencing at least one theoretical plate above the bottommost theoretical plate and ending at least one theoretical plate below the uppermost theoretical plate.

For the purposes of the present invention, pure 2-ethylhexyl acrylate and pure 2-propylheptyl acrylate is, in particular, an acrylate having a purity of in each case 98.5% by weight, in particular ≥99.5% by weight.

For the purposes of the present invention, crude alkyl acrylate is, in particular, a mixture having a content of acrylate of in each case from ≥40% by weight to ≤99% by weight, in particular from ≥60% by weight to ≤98% by weight, of 2-ethylhexyl acrylate or 2-propylheptyl acrylate. The crude 2-ethylhexyl acrylate used in the process of the invention has, in particular, the following composition:
from 40 to 99% by weight, e.g. from 70 to 99% by weight, in particular from 60 to 98% by weight, e.g. from 79 to 98% by weight, of 2-ethylhexyl acrylate,
from 0.1 to 10% by weight, in particular from 1 to 7% by weight, of 2-ethylhexanol,
from 0.1 to 10% by weight, in particular from 0.5 to 7% by weight, of relatively high boilers (relative to 2-ethylhexyl acrylate),
from 0.1 to 10% by weight, in particular from 0.5 to 7% by weight, of further low boilers (relative to 2-ethylhexyl acrylate).

The crude 2-propylheptyl acrylate used in the process of the invention has, in particular, the following composition:
from 40 to 99% by weight, e.g. from 70 to 99% by weight, in particular from 60 to 98% by weight, e.g. from 79 to 98% by weight, of 2-propylheptyl acrylate,
from 0.1 to 10% by weight, in particular from 1 to 7% by weight, of 2-propylheptanol,
from 0.1 to 10% by weight, in particular from 0.5 to 7% by weight, of relatively high boilers (relative to 2-propylheptyl acrylate), from 0.1 to 10% by weight, in particular from 0.5 to 7% by weight, of further low boilers (relative to 2-propylheptyl acrylate).

The process of the invention is carried out in a dividing wall column (1) in which a dividing wall (8) is arranged in the longitudinal direction of the column to form an upper joint column region (9), a lower joint column region (14), an inflow section (10, 12) and an offtake section (11, 13).

It has surprisingly been found that the isolation of pure 2-ethylhexyl acrylate and pure 2-propylheptyl acrylate from the corresponding crude alkyl acrylate by distillation can, contrary to the assumption that a two-stage mode of operation at different pressures is necessary, be carried out in a single column, namely a dividing wall column, and thus at a uniform pressure. A dividing wall column is a distillation column having a vertical dividing wall which, in subregions, prevents transverse mixing of liquid and vapor streams. The dividing wall, which generally consists of a flat metal sheet and can be welded, screwed or pushed in, divides the column in the longitudinal direction in its middle region into an inflow part and an offtake part.

The mixture to be fractionated, namely the corresponding crude alkyl acrylate, is fed into the inflow section and the product, namely the pure 2-ethylhexyl acrylate or correspondingly pure 2-propylheptyl acrylate, is taken off from the offtake section.

The process is preferably carried out continuously.

The dividing wall column is, like generally any distillation column, equipped with a vaporizer (bottom vaporizer) (7) and a condenser (6) at the top of the column.

In the process of the invention, the residence time in the vaporizer (7) and the associated piping system is advantageously and preferably limited to from 1 to 60 minutes, more preferably to from 10 to 30 minutes. This ensures trouble-free operation of the plant, in particular only little or no fouling, despite the polymerization susceptibility of the mixture.

In a preferred process variant, the ratio of the amount of liquid at the upper end of the dividing wall (8) going to the enrichment section (10) and the stripping section (11) of the column, i.e. amount to the enrichment section (10): amount to the stripping section (11), is set in the range from 1:0.2 to 1:5, i.e. from 5 to 0.2, preferably in the range from 1:0.5 to 1:2, i.e. from 2 to 0.5. This is preferably effected by the liquid being collected at the upper end of the dividing wall and being introduced via a regulating or adjusting device in the abovementioned ratio into the enrichment section and stripping section, respectively, of the column. This ensures a lower energy consumption.

In a further preferred process variant, the ratio of the amount of the vapor streams at the lower end of the dividing wall (8) going to the stripping section (12) and the enrichment section (13) of the column can also be set in addition to or as an alternative to regulation of the ratio of amounts of liquid runback at the upper end of the dividing wall (8). This is preferably effected by selection of the separation-active internals and/or by the additional installation of pressure drop-generating internals, for example orifice plates, or by regulation of the amounts of the vapor streams.

In a preferred process variant, the amounts of the vapor streams going to the stripping section (12) and the enrichment section (13) of the column, i.e. amount to stripping section (12): amount to enrichment section (13), is set in a ratio in the range from 1:0.5 to 1:2.0, i.e. from 2 to 0.5, preferably in a ratio in the range from 1:0.9 to 1:1.5, i.e. from 1/0.9 to 1/1.5.

The process of the invention is preferably carried out at a pressure at the top of the column of from 10 mbar to 5 bar, preferably from 10 to 100 mbar.

The upper joint column region (9) is preferably provided with temperature regulation supplying a temperature signal which can originate from a single measurement point or averaged over a plurality of measurement points below the uppermost theoretical plate, preferably at the third theoretical plate counted from the top, and utilizing as manipulated variable the distillate flow, the reflux ratio or preferably the amount of runback.

This ensures stable operation of the column, resulting in a further improvement in the achievable product purity.

In a further process variant, the lower column region is, in addition or as an alternative, provided with temperature regulation supplying a temperature signal which can originate from a single measurement point or averaged over a plurality of measurement points above the bottommost theoretical plate, preferably at the second theoretical plate counted from the bottom, and utilizing the amount taken off at the bottom as manipulated variable. A further improvement in stable column operation is achieved by means of this additional measure. Furthermore, it is possible, in addition or as an alternative, to provide level regulation which utilizes the amount taken off at the side as manipulated variable at the bottom of the column.

The ratio of the cross-sectional areas of the region of the offtake section (11, 13) to the region of the inflow section (10, 12) is preferably from 4:1 to 1:4, particularly preferably from 1.5:1 to 1:1.5, e.g. 1:1.

The dividing wall column (1) has a number of theoretical plates in the range from 10 to 60. Separation-active internals are present in the joint upper column region (9) and in the joint lower column region (14) and also in the inflow section (10, 12) and offtake section (11, 13).

The indication of the number of theoretical plates of the dividing wall column (1) always relates to the sum of the theoretical plates in the joint upper column region (9), the joint lower column region (14) and the inflow section (10, 12).

In general, the number of theoretical plates in the offtake section (11, 13) is the same as in the inflow section (10, 12), but can also be greater, e.g. greater by a factor of from 1 to 5, or smaller, e.g. smaller by a factor of from 1 to 5.

The side feed point (2) for the corresponding crude alkyl acrylate is arranged at a theoretical plate in the region commencing at least two theoretical plates above the bottommost theoretical plate and ending at least two theoretical plates below the uppermost theoretical plate, preferably at a theoretical plate in the region commencing at least four theoretical plates above the bottommost theoretical plate and ending at least four theoretical plates below the uppermost theoretical plate.

The side offtake point (3) for the pure 2-ethylhexyl acrylate or pure 2-propylheptyl acrylate is arranged at a theoretical plate in the region commencing at least two theoretical plates above the bottommost theoretical plate and ending at least two theoretical plates below the uppermost theoretical plate, preferably in the region commencing at least four theoretical plates above the bottommost theoretical plate and ending at least four theoretical plates below the uppermost theoretical plate.

The dividing wall (8) is arranged in the column in the region commencing at least one theoretical plate above the bottommost theoretical plate and ending at least one theoretical plate below the uppermost theoretical plate, preferably in the region commencing at least two theoretical plates above the bottommost theoretical plate and ending at least two theoretical plates below the uppermost theoretical plate, particularly preferably in each case centrally.

In a particularly preferred embodiment, the dividing wall column (1) has a number of theoretical plates in the range from 15 to 30, the side feed point (2) for the corresponding crude alkyl acrylate is arranged at a theoretical plate in the region commencing at least 8 theoretical plates above the bottommost theoretical plate and ending at least six theoretical plates below the uppermost theoretical plate, the side offtake point (3) for the pure 2-ethylhexyl acrylate or pure 2-propylheptyl acrylate is arranged at a theoretical plate in the region commencing at least five theoretical plates above the bottommost theoretical plate and ending at least eight theoretical plates below the uppermost theoretical plate and the dividing wall (8) in the column is arranged in the region commencing at least three theoretical plates above the bottommost theoretical plate and ending at least three theoretical plates below the uppermost theoretical plate.

In the case of equal numbers of theoretical plates in the offtake section (11, 13) and the feed section (10, 12), the side offtake point (3) can be located either at the same theoretical plate as the side feed point (2) or else below or above the side feed point; however self-evidently in each case on the other side of the dividing wall (8) (cf. FIG. 1); the opposite side offtake point (3) is preferably located below, e.g. from one to 25, in particular from 5 to 20, very particularly preferably from 6 to 15, theoretical plates below, the side feed point (2). (The theoretical plates in the column or in the column region concerned or in the column section concerned are always counted from the bottom upward.)

In the case of different numbers of theoretical plates in the feed section (11, 13) and the inflow section (10, 12), the side having the greater total number of theoretical plates in the region of the dividing wall (8) is employed for counting the number of theoretical plates for establishing the relative height position of feed point and offtake point.

There are in principle no restrictions in respect of the separation-active internals; preference is given to random packing elements and/or ordered packing and/or trays being provided.

In a further preferred process variant, dual-flow trays are used as separation-active internals in the dividing wall column. The term dual-flow tray refers in a known manner to a column tray having openings through which vapor and liquid are passed in countercurrent.

In the thermal treatment of mixtures which comprise one or more polymerizable compounds in a column, there is always the problem that the column and the column internals are fouled by deposits and have to be cleaned in a complicated fashion, resulting in operation having to be interrupted. For the present purposes, the term thermal treatment refers to processes such as distillation or rectification, absorption, extraction or stripping. Mixtures which can be subjected to thermal treatment in a column are generally fluid, i.e. gaseous, liquid or gaseous/liquid. The use of dual-flow trays reduces the fouling susceptibility of the dividing wall column compared to conventional tray columns. This increases the operating time of the column and thus makes it more economical.

Dual-flow trays are preferably used in the region of the dividing wall (10, 11, 12, 13); in a further preferred embodiment, dual-flow trays are also used in the joint upper column region (9) and in the joint lower column region (14).

A further advantageous embodiment provides for the use of dual-flow trays in the region of the dividing wall (10, 11, 12, 13) and in the joint lower column region (14) and also the use of random packing elements or ordered packing in the joint upper column region (9).

In WO 03/043712 A1 (BASF AG), it was shown for a conventional column without dividing wall that a considerable reduction in the fouling susceptibility and thus a considerably lengthening of the operating time of tray columns could be achieved by targeted selection of the diameters of the openings in the dual-flow trays.

In dividing wall columns, the same pressure drop prevails on both sides of the dividing wall. Precise setting of the gas distribution over the respective trays on the inflow side and on the offtake side by selection of the opening ratios of the trays on the inflow side and on the offtake side is of great advantage.

The gas distribution to the inflow side and the offtake side can be set precisely via targeted selection of the opening ratios. As a result of the different opening ratios of the dual-flow trays, different amounts of gas go to the two sides of the dividing wall at the same pressure drop. A complicated gas distribution facility below the dividing wall can thereby be dispensed with.

The opening ratio is set via the size and/or number of the openings. The opening ratio of a dual-flow tray is, as is known, the ratio of the sum of the areas of the openings and the total area of the dual-flow tray.

According to the invention, the openings of the dual-flow trays within a column can be made different, namely in that the diameter of the openings and/or the number of the openings are varied.

There is in principle no restriction in respect of the shape of the openings:

These can have any geometric shape, for example circles, ellipses, rectangles or polygons. The openings in the dual-flow trays are preferably circular.

A person skilled in the art can easily determine the required opening ratio as a function of gas and liquid loading and also opening diameter. The diameter of the openings in the dual-flow trays is preferably in the range from 10 to 80 mm, with dual-flow trays arranged above the feed point preferably having openings in the range from 10 to 50 mm and dual-flow trays arranged below the feed point, on the other hand, preferably having openings having diameters in the range from 15 to 80 mm.

The opening ratio of the dual-flow trays is preferably in the range from 10 to 30%.

In the process of the invention, the acrylic monomer, i.e. the 2-ethylhexyl acrylate and 2-propylheptyl acrylate, is preferably stabilized by means of suitable polymerization inhibitors in order to avoid undesirable polymerization. That is to say, the process of the invention is preferably carried out in the presence of effective amounts of a stabilizer or a plurality of stabilizers. Suitable stabilizers are in principle all polymerization inhibitors which are recommended for stabilizing (meth)acrylic acid and (meth)acrylic esters in, for example, DE 10 2005 053 982 A1 (BASF AG) and DE 102 58 329 A1 (BASF AG).

Suitable stabilizers can be, for example, N oxides (nitroxyl or N-oxyl radicals, i.e. compounds which have at least one >N—O group), e.g. 4-hydroxy-2,2,6,6-tetramethylpiperidin-N-oxyl or 4-oxo-2,2,6,6-tetramethylpiperidin-N-oxyl, phenols and naphthols such as p-methoxyphenol, p-aminophenol, p-nitrosophenol, 2-tert-butylphenol, 4-tert-butylphenol, 2,4-di-tert-butylphenol, 2-methyl-4-tert-butylphenol, 2,6-tert-butyl-4-methylphenol or 4-tert-butyl-2,6-dimethylphenol, quinones such as hydroquinone or hydroquinone monomethyl ether, aromatic amines such as N,N-diphenylamine, phenylenediamines such as N,N'-dialkyl-p-phenylenediamine, where the alkyl radicals can be identical or different and can in each case have, independently of one another, from 1 to 4 carbon atoms and be linear or branched, e.g. N,N'-dimethyl-p-phenylenediamine or N,N'-diethyl-p-phenylenediamine, hydroxylamines such as N,N-diethylhydroxylamine, imines such as methylethylimine or methylene violet, sulfonamides such as N-methyl-4-toluenesulfonamide or N-tert-butyl-4-toluenesulfonamide, oximes such as aldoximes, ketoximes or amidoximes, e.g. diethyl ketoxime, methyl ethyl ketoxime or salicylaldoxime, phosphorus-comprising compounds such as triphenyl phosphine, triphenyl phosphite or triethyl phosphite, sulfur-comprising compounds such as diphenyl sulfide or phenothiazine, metal salts such as cerium (III) acetate or cerium (III) ethylhexanoate, or mixtures thereof.

The stabilization is preferably effected by means of phenothiazine (PTZ), p-methoxyphenol (MeHQ), hydroquinone, hydroquinone monomethyl ether, 4-hydroxy-2,2,6,6-tetramethylpiperidin-N-oxyl, 4-oxo-2,2,6,6-tetramethylpiperidin-N-oxyl, 2,6-tert-butyl-4-methylphenol or mixtures thereof.

Very particular preference is given to using phenothiazine (PTZ) and/or p-methoxyphenol (MeHQ) as polymerization inhibitor.

Even though the inhibitors can be added as pure substance, it is advantageous to add the inhibitor dissolved in a solvent as solution which can be metered in simply and reproducibly, with inhibitor mixtures in a single solution also being possible in principle. Preference is given to using a liquid which is in any case present in the acrylate synthesis process or the mixture of materials in the column as solvent. Particularly preferred choices for the solvent are the acrylate product itself (here 2-ethylhexyl acrylate or 2-propylheptyl acrylate) or one of the starting materials for the synthesis of the acrylate (here acrylic acid or 2-ethylhexanol or 2-propylheptanol).

The invention will be illustrated below with the aid of a drawing (FIG. 1) and an example. The drawing shows, in the single figure, a dividing wall column 1 having a dividing wall 8 which divides the dividing wall column 1 into a joint upper column region 9, an inflow section 10 and 12 with enrichment section 10 and stripping section 12, an offtake section 11 and 13 with a stripping section 11 and an enrichment section 13, and also a joint lower column region 14. Separation-active internals are present in the column regions 9 and 14 and in the sections 10 to 13. The corresponding crude alkyl acrylate 2 enters the dividing wall column 1 between the column sections 10 and 12. The pure 2-ethylhexyl acrylate or correspondingly pure 2-propylheptyl acrylate, 3, is taken off between the column sections 11 and 13, preferably in liquid form. The vapor stream 15 obtained at the top of the column is partially condensed in the condenser 6, which is optionally supplemented by an after-condenser, and divided into the reflux stream 16 and the distillate stream 4. The uncondensed fraction from the condenser 6 comprises the low-boiling impurities and is taken off in vapor form as stream 19. At the lower end of the column, the liquid 17 is partially vaporized in a vaporizer 7 and recirculated via the pipe 18 into the column. A substream 5, which comprises the relatively high-boiling impurities, is taken off. The vaporizer 7 can be configured as a natural convection vaporizer or as forced circulation vaporizer; in the latter case, a circulation pump for the liquid stream 17 is additionally required. To avoid undesirable polymerization reactions, it is particularly advantageous to use a falling film evaporator instead of the forced circulation vaporizer since the shortest residence times are possible using such a falling film evaporator. To reduce the residence time of the liquid in the vaporizer system, it is advantageous to arrange the level regulation not in the lower column cap but instead in the feed conduit for the liquid 17.

Figure 2:
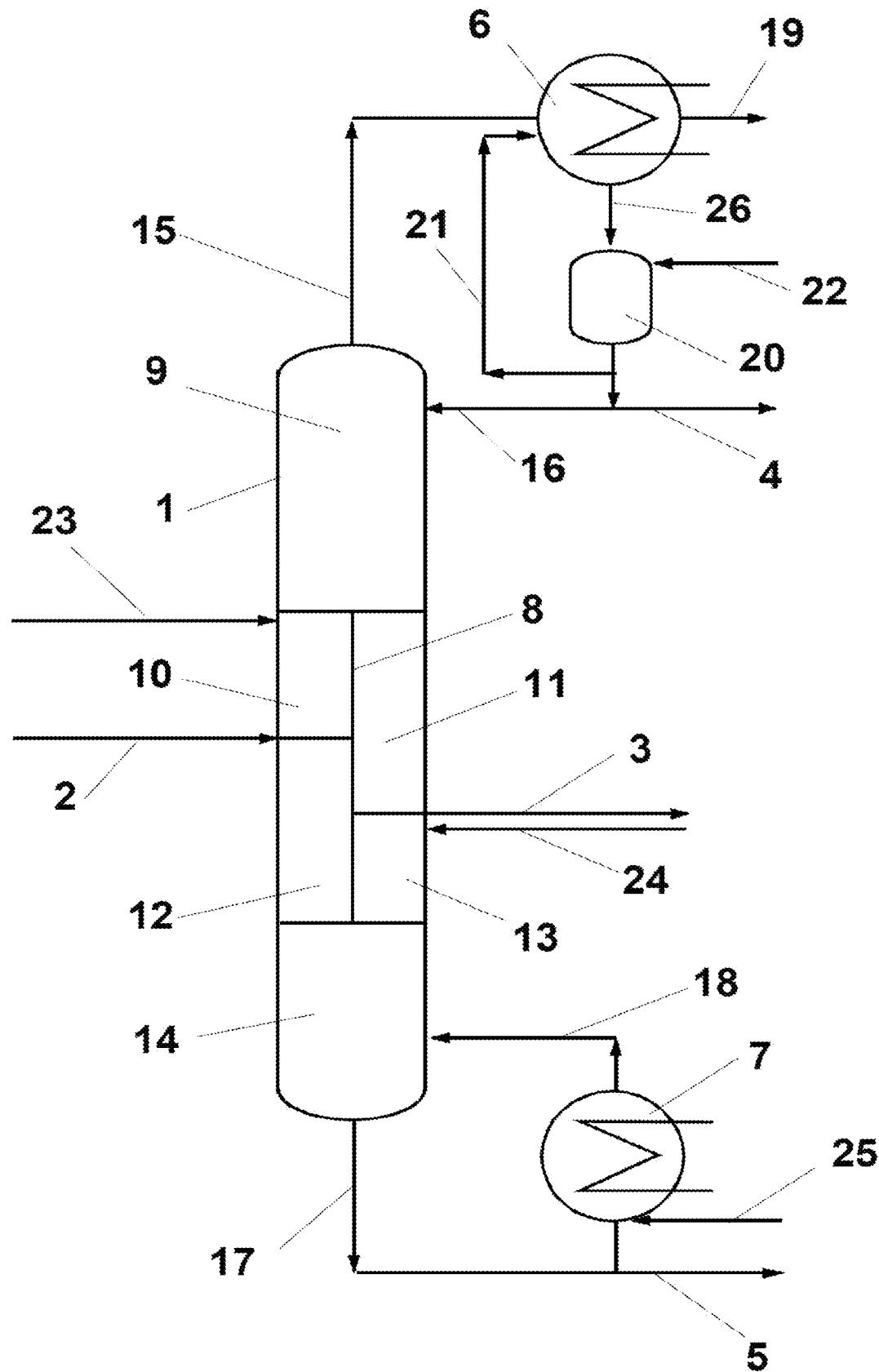

In a preferred mode of operation (cf. FIG. 2), a stabilizer 1 (23) (process stabilizer; e.g. in particular PTZ) is introduced into the enrichment section (10) of the inflow section (10, 12), there in particular just below the upper end of the dividing wall (8), in the process of the invention. The stabilizer 1 can, in particular, be used as a solution in a suitable solvent, particularly a solvent as indicated above, e.g. 2-ethylhexyl acrylate or 2-propylheptyl acrylate. In this way, the entire inflow section (10, 12) and the joint lower part of the column (14) is stabilized by means of the process stabilizer. ("Just below the upper end of the dividing wall (8)" means, for example, "from one to 5 theoretical plates below the upper end of the dividing wall (8)").

Furthermore (cf. FIG. 2), a stabilizer 2 (22) (known as storage stabilizer, e.g. in particular MeHQ) is preferably introduced into the container (20) which collects the condensate (26) and/or into the conduit of a quenching circuit (21) and/or at the top of the condenser (6) in the process of the invention. The quenching circuit which is preferably provided (i.e. the liquid return stream of part of the condensate, e.g. from 10 to 50 hundredths by weight of the condensate, into the condenser (6)) has the function of particularly satisfactorily stabilizing the naturally stabilizer-free vapors (15) during condensation in the condenser (6). The joint upper column region (9) above the dividing wall (8) and also the feed section (10, 12) and offtake section (11, 13) in the region of the dividing wall are then stabilized by means of the stabilizer (in particular MeHQ) via the return line (16), with oxygen originating from lean air also being present. The introduction of lean air (25) (mixture of air and nitrogen, in particular in such a way that an oxygen content of from 4 to 9% by volume results) occurs in particular either at the lower end of the vaporizer (7) or at the lower end of the column (1).

In a further process variant (cf. FIG. 2), process stabilizer (24), in particular PTZ, is additionally introduced into the enrichment section (13) below the side offtake point (3).

All pressures indicated are absolute pressures.

All amounts in ppm are by weight (ppm by weight).

A "low boiler" (relative to the alkyl acrylate concerned) is a material whose boiling point is lower than the boiling point of the alkyl acrylate concerned, i.e. 2-ethylhexyl acrylate or 2-propylheptyl acrylate, at the same pressure.

A "relatively high boiler" (relative to the alkyl acrylate concerned) is a material whose boiling point is higher than the boiling point of the alkyl acrylate concerned, i.e. 2-ethylhexyl acrylate or 2-propylheptyl acrylate, at the same pressure.

EXAMPLES

The modes of operation are presented with the aid of data from a thermodynamic simulation of an overall plant for preparing 2-ethylhexyl acrylate.

The thermodynamic simulation of the process was carried out using the software Aspen Plus® (Aspen for short). Aspen is comprehensive simulation software which is used for the modeling, simulation and optimization of chemical processes and plants in industry. Aspen has comprehensive modeling data banks for modeling the basic operations and also materials data banks for the materials properties of many different substances. The properties of mixtures are calculated by Aspen by means of various thermodynamic models from the materials data of the pure substances.

Example 1

(Ratio of amount of liquid at the upper end of the dividing wall (8), enrichment section (10): stripping section (11)=1:2 and ratio of amount of the vapor streams at the lower end of the dividing wall (8), stripping section (12): enrichment section (13)=1:1)

A crude 2-ethylhexyl acrylate stream of 19 180 kg/h having a temperature of 145° C. was fed in in liquid form at the 14th theoretical plate of a dividing wall column (1) having a total of 22 theoretical plates. The crude 2-ethylhexyl acrylate had the following composition:

2-Ethylhexyl acrylate: 96.3% by weight
2-Ethylhexanol: 2.5% by weight
Di-2-ethylhexyl ether: 0.2% by weight
2-Ethylhexyl acetate: 0.3% by weight
2-Ethylhexyloxy ester: 0.5% by weight
Further relatively high boilers (relative to 2-ethylhexyl acrylate): balance The dividing wall (8) extended from the 4th to the 17th theoretical plate. The side offtake (3) was located at the 6th theoretical plate. The column was operated at a pressure at the top of 22 mbar and a pressure at the bottom of 43 mbar.

At the top of the column condensation was carried out at a temperature of 26° C. A gaseous low boiler-comprising stream (19) of 5 kg/h was taken off from the condenser (6). A substream (4) of 566 kg/h was taken off from the condensed stream. The high-boiling impurities (5) were taken off at the bottom of the column at a flow rate of 1396 kg/h and a temperature of 122° C. At the side offtake, the desired product pure 2-ethylhexyl acrylate was obtained in liquid form at a temperature of 117° C. in an amount of 17 213 kg/h.

The side offtake stream (3) had the following composition:

2-Ethylhexyl acrylate: 99.98% by weight
2-Ethylhexanol: 0.05% by weight
Di-2-ethylhexyl ether: 62 ppm by weight
2-Ethylhexyl acetate: 855 ppm by weight
2-Ethylhexyloxy ester: <0.01% by weight
Further relatively high boilers (relative to 2-ethylhexyl acrylate): balance The minimum content of acrylate of >99.5% by weight and the commercial specifications for the secondary components 2-ethylhexyl acetate at 1000 ppm and for di-2-ethylhexyl ether at 100 ppm are adhered to.

The distillation yield for 2-ethylhexyl acrylate was more than 93%.

The ratio of amounts of liquid for the liquid at the upper end of the dividing wall (8), enrichment section (10): stripping section (11), was 1:2. At the lower end of the dividing wall (8), the amounts of vapor stream, stripping section (12): enrichment section (13), were divided in the ratio 1:1. The heating power of the vaporizer was 2175 kW.

The process of the invention enabled the distillation of crude 2-ethylhexyl acrylate to give pure 2-ethylhexyl acrylate to be carried out, for example, at an annual capacity of 130 000 metric tons while adhering to the required specifications with a capital cost saving of 25% and an energy cost saving of 32% compared to a conventional two-stage distillation process.

Comparative Example 1

(Ratio of amount of liquid at the upper end of the dividing wall (8), enrichment section (10): stripping section (11)=1:7 and ratio of amount of vapor streams at the lower end of the dividing wall (8), stripping section (12): enrichment section (13)=1:1)

A crude 2-ethylhexyl acrylate stream of 19 180 kg/h having a temperature of 145° C. was fed in in liquid form at the 14th theoretical plate of a dividing wall column (1) having a total of 22 theoretical plates. The crude 2-ethylhexyl acrylate had the following composition:

2-ethylhexyl acrylate: 96.3% by weight
2-ethylhexanol: 2.5% by weight
Di-2-ethylhexyl ether: 0.2% by weight
2-ethylhexyl acetate: 0.3% by weight
2-ethylhexyloxy ester: 0.5% by weight
Further relatively high boilers (relative to 2-ethylhexyl acrylate): balance The dividing wall (8) extended from the 4th to the 17th theoretical plate. The side offtake (3) was located at the 6th theoretical plate. The column was operated at a pressure at the top of 22 mbar and a pressure at the bottom of 43 mbar.

At the top of the column, condensation was carried out at a temperature of 26° C. A gaseous low boiler-comprising stream (19) of 5 kg/h was taken off from the condenser (6). A substream (4) of 123 kg/h was taken off from the condensed stream. The high-boiling impurities (5) were taken off at the bottom of the column at a flow rate of 1838 kg/h and a temperature of 122° C. At the side offtake, the desired product pure 2-ethylhexyl acrylate was obtained in liquid form at a temperature of 116° C. in an amount of 17 213 kg/h.

The side offtake stream (3) had the following composition:

2-Ethylhexyl acrylate: 97.61% by weight
2-Ethylhexanol: 2.06% by weight
Di-2-ethylhexyl ether: 26 ppm by weight
2-Ethylhexyl acetate: 3312 ppm by weight
2-Ethylhexyloxy ester: <0.01% by weight
Further relatively high boilers (relative to 2-ethylhexyl acrylate): balance The minimum content of acrylate of >99.5% by weight and the commercial specification for the secondary component 2-ethylhexyl acrylate at 1000 ppm are not adhered to.

The distillation yield for 2-ethylhexyl acrylate was more than 90%.

The ratio of amounts of liquid for the liquid at the upper end of the dividing wall (8), enrichment section (10): stripping section (11), was 1:7. At the lower end of the dividing wall (8), the amounts of vapor stream, stripping section (12): enrichment section (13), were divided in the ratio 1:1. The heating power of the vaporizer was 2875 kW.

Comparative Example 2

(Ratio of amount of liquid at the upper end of the dividing wall (8), reinforcement section (10): stripping section (11)=1:2 and ratio of amounts of the vapor streams at the lower end of the dividing wall (8), stripping section (12): enrichment section (13)=3:1)

A crude 2-ethylhexyl acrylate stream of 19 180 kg/h having a temperature of 145° C. was fed in in liquid form at the 14th theoretical plate of a dividing wall column (1)

having a total of 22 theoretical plates. The crude 2-ethylhexyl acrylate had the following composition:
2-Ethylhexyl acrylate: 96.3% by weight
2-Ethylhexanol: 2.5% by weight
Di-2-ethylhexyl ether: 0.2% by weight
2-Ethylhexyl acetate: 0.3% by weight
2-Ethylhexyloxy ester: 0.5% by weight
Further relatively high boilers (relative to 2-ethylhexyl acrylate): balance The dividing wall (8) extended from the 4th to the 17th theoretical plate. The side offtake (3) was located at the 6th theoretical plate. The column was operated at a pressure at the top of 22 mbar and a pressure at the bottom of 43 mbar.

At the top of the column, condensation was carried out at a temperature of 26° C. A gaseous low boiler-comprising stream (19) of 5 kg/h was taken off from the condenser (6). A substream (4) of 498 kg/h was taken off from the condensed stream. The high-boiling impurities (5) were taken off at the bottom of the column at a flow rate of 1463 kg/h and a temperature of 122° C. At the side offtake, the desired product pure 2-ethylhexyl acrylate was obtained in liquid form at a temperature of 117° C. in an amount of 17 213 kg/h.

The side offtake stream (3) had the following composition:
2-Ethylhexyl acrylate: 99.49% by weight
2-Ethylhexanol: 0.39% by weight
Di-2-ethylhexyl ether: 121 ppm by weight
2-Ethylhexyl acetate: 1039 ppm by weight
2-Ethylhexyloxy ester: <0.01 ppm by weight
Further relatively high boilers (relative to 2-ethylhexyl acrylate): balance The minimum content of acrylate of >99.5% by weight and the commercial specifications for the secondary components 2-ethylhexyl acetate at 1000 ppm and for di-2-ethylhexyl ether at 100 ppm are not adhered to.

The distillation yield for 2-ethylhexyl acrylate was more than 92%.

The ratio of amounts of liquid for the liquid at the upper end of the dividing wall (8), enrichment section (10): stripping section (11), was 1:2. At the lower end of the dividing wall (8), the amounts of vapor stream, stripping section (12): enrichment section (13), were divided in the ratio 3:1. The heating power of the vaporizer was 2175 kW.

The invention claimed is:

1. A process for purifying 2-propylheptyl acrylate from a corresponding crude alkyl acrylate, the process comprising:
distilling the corresponding crude alkyl acrylate in a dividing wall column,
wherein the dividing wall column has separation-active internals and a vaporizer and in which a dividing wall is arranged in a longitudinal direction of the dividing wall column to form an upper joint column region, a lower joint column region, an inflow section having a side feed point and a side offtake section having a side offtake point,
wherein the dividing wall column has a number of theoretical plates in the range from 10 to 60, where the number of theoretical plates of the dividing wall column relates to the sum of the theoretical plates in the joint upper column region, the joint lower column region and the inflow section,
wherein in the dividing wall column the side feed point for the corresponding crude alkyl acrylate is arranged at a theoretical plate in a region commencing at least two theoretical plates above a bottommost theoretical plate and ending at least two theoretical plates below an uppermost theoretical plate, the side offtake point for a distilled 2-propylheptyl acrylate is arranged at a theoretical plate in the region commencing at least two theoretical plates above the bottommost theoretical plate and ending at least two theoretical plates below the uppermost theoretical plate, and the dividing wall is arranged in the dividing wall column in a region commencing at least one theoretical plate above the bottommost theoretical plate and ending at least one theoretical plate below the uppermost theoretical plate,
where a ratio of an amount of liquid at the upper end of the dividing wall going to an enrichment section and an amount of liquid at a stripping section of the dividing wall column is in the range from 1:0.2 to 1:5 and a ratio of amounts of a vapor stream at the lower end of the dividing wall going to the stripping section and a vapor stream at the enrichment section of the dividing wall column is in the range from 1:0.5 to 1:2.0, wherein the upper end is above the side feed point and the lower end is below the side offtake point; and
wherein the distilling includes isolating 2-propylheptyl acrylate having a purity of ≥98.5% by weight from the corresponding crude alkyl acrylate.

2. The process according to claim 1, wherein the side feed point for the corresponding crude alkyl acrylate is arranged at a theoretical plate in a region commencing at least four theoretical plates above the bottommost theoretical plate and ending at least four theoretical plates below the uppermost theoretical plate, the side offtake point for the distilled 2-propylheptyl acrylate is arranged at a theoretical plate in the region commencing at least four theoretical plates above the bottommost theoretical plate and ending at least four theoretical plates below the uppermost theoretical plate and the dividing wall in the dividing wall column is arranged in the region commencing at least two theoretical plates above the bottommost theoretical plate and ending at least two theoretical plates below the uppermost theoretical plate.

3. The process according to claim 1, wherein the dividing wall column has a number of theoretical plates in the range from 15 to 30, the side feed point for the corresponding crude alkyl acrylate is arranged at a theoretical plate in a region commencing at least eight theoretical plates above the bottommost theoretical plate and ending at least six theoretical plates below the uppermost theoretical plate, the side offtake point for the distilled 2-propylheptyl acrylate is arranged at a theoretical plate in a region commencing at least five theoretical plates above the lowermost theoretical plate and ending at least eight theoretical plates below the uppermost theoretical plate and the dividing wall in the column is arranged in a region commencing at least three theoretical plates above the bottommost theoretical plate and ending at least three theoretical plates below the uppermost theoretical plate.

4. The process according to claim 1, wherein an opposite side offtake point is located at least one theoretical plate below the side feed point, where in the case of different numbers of theoretical plates in the side offtake section and the inflow section, the side having the greatest total number of theoretical plates in the region of the dividing wall is a basis for counting the number of theoretical plates for determining the relative height position of the feed point and the offtake point.

5. The process according to claim 1, wherein the dividing wall column comprises one or more separation-active internals selected from the group consisting of a random packing element, an ordered packing and a tray.

6. The process according to claim 5, wherein the dividing wall column comprises dual-flow trays.

7. The process according to claim 6, wherein dual-flow trays on the inflow side and dual-flow trays on the offtake side have different opening ratios for gas distribution.

8. The process according to claim 1, wherein during the distilling a residence time of material in the vaporizer and piping in proximity of and fluidly connected to the vaporizer is from 1 to 60 minutes.

9. The process according to claim 1, wherein the ratio of the amount of the liquid at the upper end of the dividing wall going to the enrichment section and the amount of the liquid going to the stripping section of the dividing wall column is in the range from 1:0.5 to 1:2.

10. The process according to claim 1, wherein the ratio of the amount of the vapor stream at the lower end of the dividing wall going to the stripping section and the amount of the vapor stream at the enrichment section of the dividing wall column is in the range from 1:0.9 to 1:1.5.

11. The process according to claim 1, wherein during the distilling a pressure at the top of the dividing wall column is in the range from 10 mbar to 5 bar.

12. The process according to claim 1, wherein the dividing wall column further comprises a temperature controller in the upper joint column region, wherein the temperature controller receives a temperature signal below the uppermost theoretical plate, and the process further comprises:
changing at least one of a distillate flow, a reflux ratio and an amount of reflux.

13. The process according to claim 1, wherein the dividing wall column further comprises a temperature controller in the lower joint column region, wherein the temperature controller receives a temperature signal above the bottommost theoretical plate, and the process further comprises:
changing an amount of material taken off at the bottom of the dividing wall column.

14. The process according to claim 1, wherein the dividing wall column further comprises a level controller at the bottom of the dividing wall column, and the process further comprises:
changing an amount of material taken off at the side of the dividing wall column.

15. The process according to claim 1, wherein a ratio of a cross-sectional area of a region of the offtake section to a cross-sectional area of a region of the inflow section is from 4:1 to 1:4.

16. The process according to claim 1, wherein a ratio of a cross-sectional area of a region of the offtake section to a cross-sectional area of a region of the inflow section is from 1.5:1 to 1:1.5.

17. The process according to claim 1, wherein the corresponding crude alkyl acrylate has the following composition:
from 40 to 99% by weight of 2-propylheptyl acrylate,
from 0.1 to 10% by weight of 2-propylheptanol,
from 0.1 to 10% by weight of high boilers having a boiling point greater than the boiling point of 2-propylheptyl acrylate, and
from 0.1 to 10% by weight of low boilers having a boiling point less than the boiling point of 2-propylheptyl acrylate.

18. The process according to claim 1, further comprising:
introducing a stabilizer 1 into the enrichment section of the inflow section.

19. The process according to claim 18, wherein the stabilizer 1 is phenothiazine (PTZ).

20. The process according to claim 1, further comprising:
introducing a stabilizer 2 into a container which collects a condensate and/or into a quenching conduit.

21. The process according to claim 20, wherein the stabilizer 2 is p-methoxyphenol (MeHQ).

22. A process for purifying 2-ethylhexyl acrylate from a corresponding crude alkyl acrylate, the process comprising:
distilling the corresponding crude alkyl acrylate in a dividing wall column,
wherein the dividing wall column has separation-active internals and a vaporizer and in which a dividing wall is arranged in a longitudinal direction of the dividing wall column to form an upper joint column region, a lower joint column region, an inflow section having a side feed point and a side offtake section having a side offtake point,
wherein the dividing wall column has a number of theoretical plates in the range from 10 to 60, where the number of theoretical plates of the dividing wall column relates to the sum of the theoretical plates in the joint upper column region, the joint lower column region and the inflow section,
wherein in the dividing wall column the side feed point for the corresponding crude alkyl acrylate is arranged at a theoretical plate in a region commencing at least two theoretical plates above a bottommost theoretical plate and ending at least two theoretical plates below an uppermost theoretical plate, the side offtake point for a distilled 2-ethylhexyl acrylate is arranged at a theoretical plate in the region commencing at least two theoretical plates above the bottommost theoretical plate and ending at least two theoretical plates below the uppermost theoretical plate, and the dividing wall is arranged in the dividing wall column in a region commencing at least one theoretical plate above the bottommost theoretical plate and ending at least one theoretical plate below the uppermost theoretical plate,
where a ratio of an amount of liquid at the upper end of the dividing wall going to an enrichment section and an amount of liquid at a stripping section of the dividing wall column is in the range from 1:0.2 to 1:5 and a ratio of amounts of a vapor stream at the lower end of the dividing wall going to the stripping section and a vapor stream at the enrichment section of the dividing wall column is in the range from 1:0.5 to 1:2.0, wherein the upper end is above the side feed point and the lower end is below the side offtake point; and
wherein the distilling includes isolating 2-ethylhexyl acrylate having a purity of ≥98.5% by weight from the corresponding crude alkyl acrylate, and
wherein the corresponding crude alkyl acrylate has the following composition:
from 40 to 99% by weight of 2-ethylhexyl acrylate,
from 0.1 to 10% by weight of 2-ethylhexanol,
from 0.1 to 10% by weight of high boilers having a boiling point greater than the boiling point of 2-ethylhexyl acrylate, and
from 0.1 to 10% by weight of low boilers having a boiling point less than the boiling point of 2-ethylhexyl acrylate.

23. The process according to claim 22, wherein the side feed point for the corresponding crude alkyl acrylate is arranged at a theoretical plate in a region commencing at least four theoretical plates above the bottommost theoretical plate and ending at least four theoretical plates below the uppermost theoretical plate, the side offtake point for the distilled 2-ethylhexyl acrylate is arranged at a theoretical plate in the region commencing at least four theoretical plates above the bottommost theoretical plate and ending at least four theoretical plates below the uppermost theoretical plate and the dividing wall in the dividing wall column is arranged in the region commencing at least two theoretical plates above the bottommost theoretical plate and ending at least two theoretical plates below the uppermost theoretical plate.

24. The process according to claim 22, wherein the dividing wall column has a number of theoretical plates in the range from 15 to 30, the side feed point for the corresponding crude alkyl acrylate is arranged at a theoretical plate in a region commencing at least eight theoretical plates above the bottommost theoretical plate and ending at least six theoretical plates below the uppermost theoretical plate, the side offtake point for the distilled 2-ethylhexyl acrylate is arranged at a theoretical plate in a region commencing at least five theoretical plates above the lowermost theoretical plate and ending at least eight theoretical plates below the uppermost theoretical plate and the dividing wall in the column is arranged in a region commencing at least three theoretical plates above the bottommost theoretical plate and ending at least three theoretical plates below the uppermost theoretical plate.

25. The process according to claim 22, wherein an opposite side offtake point is located at least one theoretical plate below the side feed point, where in the case of different numbers of theoretical plates in the side offtake section and the inflow section, the side having the greatest total number of theoretical plates in the region of the dividing wall is a basis for counting the number of theoretical plates for determining the relative height position of the feed point and the offtake point.

26. The process according to claim 22, wherein the dividing wall column comprises one or more separation-active internals selected from the group consisting of a random packing element, an ordered packing and a tray.

27. The process according to claim 26, wherein the dividing wall column comprises dual-flow trays.

28. The process according to claim 27, wherein dual-flow trays on the inflow side and dual-flow trays on the offtake side have different opening ratios for gas distribution.

29. The process according to claim 22, wherein during the distilling a residence time of material in the vaporizer and piping in proximity of and fluidly connected to the vaporizer is from 1 to 60 minutes.

30. The process according to claim 22, wherein the ratio of the amount of the liquid at the upper end of the dividing wall going to the enrichment section and the amount of the liquid going to the stripping section of the dividing wall column is in the range from 1:0.5 to 1:2.

31. The process according to claim 22, wherein the ratio of the amount of the vapor stream at the lower end of the dividing wall going to the stripping section and the amount of the vapor stream at the enrichment section of the dividing wall column is in the range from 1:0.9 to 1:1.5.

32. The process according to claim 22, wherein during the distilling a pressure at the top of the dividing wall column is in the range from 10 mbar to 5 bar.

33. The process according to claim 22, wherein the dividing wall column further comprises a temperature controller in the upper joint column region, wherein the temperature controller receives a temperature signal below the uppermost theoretical plate, and the process further comprises:
changing at least one of a distillate flow, a reflux ratio and an amount of reflux.

34. The process according to claim 22, wherein the dividing wall column further comprises a temperature controller in the lower joint column region, wherein the temperature controller receives a temperature signal above the bottommost theoretical plate, and the process further comprises:
changing an amount of material taken off at the bottom of the dividing wall column.

35. The process according to claim 22, wherein the dividing wall column further comprises a level controller at the bottom of the dividing wall column, and the process further comprises:
changing an amount of material taken off at the side of the dividing wall column.

36. The process according to claim 22, wherein a ratio of a cross-sectional area of a region of the offtake section to a cross-sectional area of a region of the inflow section is from 4:1 to 1:4.

37. The process according to claim 22, wherein a ratio of a cross-sectional area of a region of the offtake section to a cross-sectional area of a region of the inflow section is from 1.5:1 to 1:1.5.

38. The process according to claim 22, further comprising:
introducing a stabilizer 1 into the enrichment section of the inflow section.

39. The process according to claim 38, wherein the stabilizer 1 is phenothiazine (PTZ).

40. The process according to claim 22, further comprising:
introducing a stabilizer 2 into a container which collects a condensate and/or into a quenching conduit.

41. The process according to claim 40, wherein the stabilizer 2 is p-methoxyphenol (MeHQ).

* * * * *